United States Patent [19]

Jones, Jr. et al.

[11] Patent Number: 4,769,380

[45] Date of Patent: Sep. 6, 1988

[54] CARDIOTONIC 5-BENZOYL-1,2-DIHYDRO-2-OXO-3-PYRIDINECARBOXYLATES

[75] Inventors: Winton D. Jones, Jr.; Richard A. Dage; Richard A. Schnettler, all of Cincinnati, Ohio

[73] Assignee: Merrell Dow Pharmaceuticals Inc., Cincinnati, Ohio

[21] Appl. No.: 892,215

[22] Filed: Jul. 31, 1986

Related U.S. Application Data

[63] Continuation-in-part of Ser. No. 594,767, Mar. 29, 1984, abandoned, which is a continuation-in-part of Ser. No. 490,081, Apr. 29, 1983, Pat. No. 4,568,751.

[51] Int. Cl.$^4$ .................. C07D 211/86; C07D 401/06; A61K 31/455
[52] U.S. Cl. ..................................... 514/341; 514/342; 514/343; 514/346; 514/350; 546/261; 546/281; 546/283; 546/284; 546/276; 546/298; 546/299
[58] Field of Search ............. 546/298, 261, 276, 281, 546/283, 284, 299; 514/341, 342, 343, 350, 346

[56] References Cited

U.S. PATENT DOCUMENTS 3,769,291 10/1973 Parker et al. .................... 546/288
4,347,363 8/1982 Singh .................................. 546/249

FOREIGN PATENT DOCUMENTS 0061774 3/1982 European Pat. Off. ............ 546/288

OTHER PUBLICATIONS

Jaques et al., Chem. Abstracts (9), Abst. No. 56686k, Aug. 6, 1972.
Sunthankar, Chem. Abstracts, vol. 80(23), Abst. No. 133,202r, Jun. 10, 1974.
Crombie et al., Chem. Abstracts, vol. 91(15), Abst. No. 123,613p, Oct. 8, 1979.
Sunthankar, Chem. Abstracts, vol. 93(11), Abst. No. 114,281t, Sep. 15, 1980.
CA, 83:206076b provided. T. Hatada et al., *Yakugaku Zasshi*, 95(6), 623–28 (1975).
CA, 93:71644u provided. M. Augustin, S. Bielka, *Z. Chem.*, 20(3), 96–7 (1980).
Baker, S. R. et al., *J. Chem. Soc.*, Perkin Trans. 1(3), 677–85 (1979).

*Primary Examiner*—Alan L. Rotman
*Attorney, Agent, or Firm*—Stephen L. Nesbitt

[57] ABSTRACT

Novel 3-carboxy- and 3-carbalkoxy-5-benzoyl-2(1H)-pyridinones as well as the pharmaeutically acceptable salts thereof are cardiotonic agents useful in the treatment of heart failure.

6 Claims, No Drawings

CARDIOTONIC 5-BENZOYL-1,2-DIHYDRO-2-OXO-3-PYRIDINECARBOXYLATES

This is a continuation-in-part application of U.S. application Ser. No. 594,767, filed Mar. 29, 1984, now abandoned which is a continuation-in-part application of U.S. application Ser. No. 490,081, filed Apr. 29, 1983, now U.S. Pat. No. 4,568,751.

This invention relates to 5-acyl-2-(1H)-pyridinones and to their use as cardiotonic agents.

More specifically, this invention relates to pharmaceutically active 5-acyl-2-(1H)-pyridinones of the formula

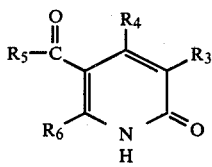

and the pharmaceutically acceptable salts thereof, wherein $R_3$ is H, —C≡N, $NH_2$, $CONH_2$ and COOR with R being hydrogen or lower alkyl, $R_4$ is hydrogen or lower alkyl, $R_5$ is phenyl, X-substituted phenyl, pyridyl, thienyl, furyl, pyrrolyl and OR wherein R is hydroxy or lower alkoxy, and X is lower alkyl, lower alkoxy, lower alkyl thio, halogen, nitro, lower alkanoyl, alkoxy carbonyl, carboxy, cyano, $NH_2$, $CONH_2$, amidino, imidazol-2-yl, and $CF_3$, and $R_6$ is hydrogen, methyl, ethyl or $R_5$. These compounds are useful as cardiotonics in the treatment of cardiac failure and other conditions requiring strengthening of heart action with a cardiotonic agent.

As used herein, the term "alkyl" includes straight, branched-chain or cyclized hydrocarbyl radicals. The term "X-substituted phenyl" includes those substituents, preferably located in the para position but includes the ortho and meta substituted compounds. The term "lower" when used to modify alkyl, alkoxy, alkylthio embrace those radicals having one to six carbon atoms. Inclusive of other "X" radicals are alkoxycarbonyl (—COO lower alkyl), lower alkanoyl (—CO-lower alkyl),

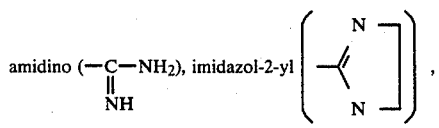

and halogeno preferably includes chloro and bromo but is embrasive of all members. The term "pyridyl" includes 2-, 3-, and 4-pyridyl, "furanyl" includes 2- an 3-furanyl, "thienyl" includes 2- and 3-thienyl, and "pyrryl" includes 2- and 3-(1H) pyrryl.

The compounds of formula I are useful both in the free base form and in the form of acid addition salts with both forms being within the purview of this invention. The acid addition salts are simply a more convenient form for use and, in practice, use of the salt amounts to use of the free base. The acids which can be used include those which produce, when combined with the free base, pharmaceutically acceptable salts, that is salts whose anions are relatively inocuous to the animal organism in pharmaceutical doses of the salts. In practice, it is convenient to form sulfate, phosphate, methansulfate or laetate salts. Others are those derived from mineral acids (e.g., hydrochloric), and organic acids such as acetic acid, citric acid, tartaric acid, ethanesulfonic acid, benzenesulfonic acid, p-toluenesulfonic acid and the like. The acid salts are prepared by standard techniques such as by dissolving the free base in aqueous of aqueous-alcohol solution or other suitable solvents containing the appropriate acid and isolating by evaporating the solution, or by reacting the free base and in an organic solvent in which case the salt separates directly or can be obtained by concentration of the solution.

In general, the compounds of this invention are prepared by standard techniques analogously known in the art. A preferred synthesis for preparing the compounds of this invention conveniently involves the reaction of an appropriate 1-$R_5$-3-$R_6$-2-(1-dimethylamino-1-$R_4$-methylidenyl)-1,3-propanedione (II) with an appropriately $R_3$ substituted acetoacetamide according to standard Michael addition reaction conditions. Preferably, the substituted acetamide is reacted with sodium hydride, under argon in an inert organic solvent, (e.g., tetrahydrofuran) to form an anion which is then condensed with the diketone (II) by heating the reactants together in an inert organic solvent, preferably tetrahydrofuran and the like. Preferaby, the temperature of the reaction is about 50° C. although the reaction proceeds well at temperatures between room temperature and 100° C. Heating is effected over a period of several hours although it preferred to allow the reaction to proceed overnight. When $R_5$ and $R_6$ are not the same a mixture of products are obtained which are separated quite nicely by flash chromatography wherein the reaction product mixture is admixed with 60–200 mesh silica gel and the column is eluted with an appropriate solvent system (e.g., 35% ethylacetate - 65% methylene chloride). The fractions of eluate are monitored by thin layer chromatography.

The foregoing reaction is depicted as follows:

Reaction Scheme A:

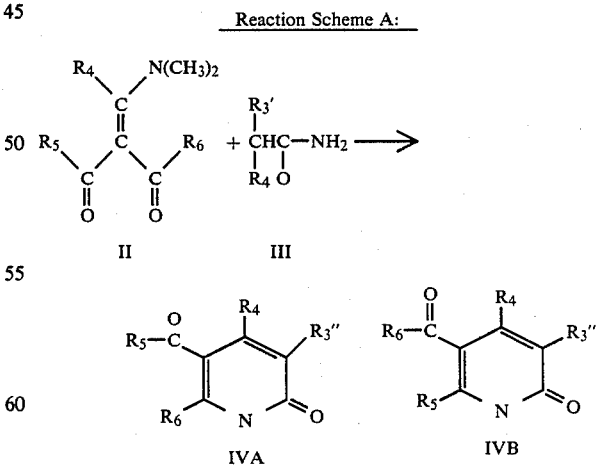

wherein $R_4$, $R_5$ and $R_6$ are as previously defined, $R_3''$ is cyano, —$CO_2H$, lower alkyl or $NH_2$; $R_3'$ is cyano, —$CO_2H$, lower alkyl or —N=CH phenyl.

The 1-$R_5$-3$R_6$-2-[(1-dimethylamino)alkylidenyl]-1,3-propanediones are readily prepared by condensing the appropriate $R_5$, $R_6$-1,3-propandiones with the appropriately $R_4$ substituted N,N-dialkylamino-dialkoxy methane (e.g., dimethylformamide acetals according to standard condensation reaction conditions such as, for example, contacting equimolar quantities of the reactants together, optionally in an inert organic solvent and stirring the mixture for 1-12 hours at about room temperature. This reaction is depicted as follows:

Reaction Scheme B:

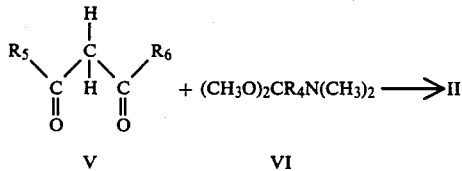

wherein $R_4$, $R_5$ and $R_6$ are as previously defined.

In those instances, wherein X is other than lower alkyl, hydroxy, alkoxy, halogen, nitro, cyano, amino, and $R_3$ is other than cyano, it is preferred to prepare a compound of formula I wherein X is cyano, and then, by the use of standard techniques, convert the cyano moiety to the desired substituents. For example, the cyano moiety may be converted to a carboxyl moiety by hydrolyzing the nitrile with 6N hydrochloric acid, sulfuric and/or other mineral acids under standard conditions such as by heating at reflux temperatures for about 12-24 hours. The carboxyl moiety may be converted to an alkoxycarbonyl moiety by the standard Fisher esterification procedure such as by heating the carboxy-containing compounds with an appropriate alcohol in the presence of an acid, e.g., 3% hydrochloric acid. The carboxamido-containing compounds may be prepared by converting the alkoxycarbonyl moiety by heating the esters in the presence of ammonia or an appropriate amine, preferably in a pressure bomb at about 100°-150° C. in an inert solvent, e.g., benzene, toluene and the like. Alternatively, the carboxamido moiety may be prepared by hydrolyzing a nitrile with concentrated sulfuric acid by heating on a steam bath at temperatures of about 50°-100° C. In those instances wherein $R_3$ is cyano, it is preferred to have the ultimately desired X substituent on the phenyl ring prior to the Michael addition reaction between the 1-$R_5$-3-$R_6$-2-(1-dimethylamino-1-$R_4$-methylidenyl)-1,3-propanedione and the cyano substituted acetamide.

In those instances wherein X is imidazol-2-yl, such compounds are prepared by a condensation reaction wherein the nitrile is heated to from about 150°-200° C. with ethylene diamine for about 2 hours. The amidino compounds are prepared from corresponding nitriles wherein the nitrile is converted to an imino ether which is converted to the amidino moiety by treating the imino ether with ammonia in alcohol at temperatures of about 0° C. room temperature.

In those instances wherein the $R_3$ substituent is hydrogen, it is preferred to chemically remove a cyano moiety from a compound of formula I by standard techniques such as by conversion of the cyano moiety to a carboxyl radical by treatment with a strong acid and then the compound is decarboxylated.

The preparation of the compounds of formula I may be illustrated by the following specific examples.

PREPARATION OF INTERMEDIATE 1-$R_5$-3$R_6$-2-(1-DIALKYLAMINO-1-$R_4$ METHYLIDINYL)-1,3-PROPANDIONES

EXAMPLE 1

2-Dimethylaminomethylenyl-1-phenyl-1,3-butandione

A mixture of 1-benzoylacetone (24.00 g, 0.15 mole) and dimethylformamide dimethylacetal were stirred overnight at room temperature under argon. The resulting reddish-colored mixture was concentrated on the rotary evaporator, then dissolved in THF (tetrahydrofuran). The resulting solution was stirred and heated to boiling the slowly diluted with hexane. At the point of turbidity heating was discontinued. An orange gum precipitated and rapidly solidified. The mixture was chilled in an ice bath and filtered yielding 25.5 g (78%) of 2-(dimethylamino)-1-phenyl-1,3-butanedione m.pt. 72°-74° C.

In a similar manner, by substituting the 1,3-propandiones of the foregoing example with the appropriately substituted analogs thereof and by substantially following the procedures there is produced the following intermediates:

1-(4-pyridyl)-2-(dimethylaminomethylenyl)-1,3-butandione;

1-(2-thienyl)-2-(dimethylaminomethylenyl)-1,3-butandione;

1-[2-(1-H-pyrryl)]-2-(dimethylaminomethylenyl)-1,3-butandione;

1-(3-furanyl)-2-(dimethylaminomethylenyl)-1,3-butandione;

1-(4-methoxyphenyl)-2-(dimethylaminomethylenyl)-1,3-butandione;

1-(4-methylphenyl)-2-(dimethylaminomethylenyl)-1,3-butandione;

1-(4-nitrophenyl)-2-(dimethylaminomethylenyl)-1,3-butandione;

1-(4-aminophenyl)-2-(dimethylaminomethylenyl)-1,3-butandione;

1-(2,4-dichlorophenyl)-2-(dimethylaminomethylenyl)-1,3-butandione;

1-(4-cyanophenyl)-2-(dimethylaminomethylenyl)-1,3-butandione.

PREPARATION OF THE FINAL PRODUCTS

EXAMPLE 2

5-Acetyl-1,2-dihydro-2-oxo-6-phenyl-3-pyridinecarbonitrile

Cyanoacetamide (2.50 g, 0.03 mole) was added to a stirred suspension of sodium hydride in (150 ml) THF and warmed to 50° C. The mixture was allowed to cool to room temperature then 3-[(dimethylamino)methylenyl]-1-phenyl-1,3-butanedione (6.25 g, 0.03 mole) dissolved in THF (20 ml) was added all at once. The suspension was heated and stirred at 50° C. overnight. The reaction mixture was allowed to cool to room temperature, treated with acetic acid to pH 6 and concentrated on the rotary evaporator. Workup as in Example 5 gave 3.0 g of a yellow powder. The powder was mixed with 10 g of silica gel (60-200 mesh) and flash chromatographed eluting with 25% EtOAC -75% $CH_2Cl_2$ collecting 50 ml fractions to yield 1.1 g of 5-acetyl-1,2-dihydro-2-oxo-6-phenyl-3-pyridinecarbonitrile m.pt. 259°-261° C. in fractions 11 to 20.

EXAMPLE 3

5-Benzoyl-1,2-dihydro-6-methyl-2-oxo-3-pyridinecarbonitrile

The chromatography in Example 6 gave 1.1 g of 5-benzoyl-1,2-dihydro-6-methyl-2-oxo-3-pyridinecarbonitrile in fractions 24 to 40 m.pt. 260°–261° C.

EXAMPLE 4

3-Cyano-1,2-dihydro-6-methyl-2-oxo-5-pyridinecarboxylic acid ethyl ester

Ethylacetoacetate (6.5 g, 0.050 mole) and dimethylformamide dimethyl acetal (7.14 g, 0.060 mole) were stirred together under argon overnight. The resulting reddish oil was concentrated on the rotary evaporator and the concentrate then dissolved in THF (10 ml) and quickly added to a suspension of cyanoacetamide (4.20 g, 0.050 mole) and sodium hydride in THF (175 ml). The reaction mixture was neutralized to pH 6 with acetic acid and concentrated on the rotary evaporator. The residue was triturated with a 50:50 $CH_2Cl_2$-$H_2O$ mixture collected and recrystallized (EtOAC) giving 4.7 g of 3-cyano-1,2-dihydro-6-methyl-2-oxo-5-pyridinecarboxylic acid ethyl ester m.pt. 208°–210° C.

EXAMPLE 5

6-Ethyl-1,2-dihydro-5-[(4-methylthio)benzoyl]-2-oxo-3-pyridinecarbonitrile and
5-(1-oxopropyl)-1,2-dihydro-6-(4-methylthiophenyl)-2-oxo-3-pyridinecarbonitrile 1-[4-((Methylthio)phenyl)]-1,3-pentanedione (2.66 g, 0.12 mole) and dimethylformamide dimethylacetal (1.79 g, 0.015 mole) were stirred overnight at room temperature. The resulting red oil was concentrated on the rotary evaporator and the concentrate was dissolved in THF and added to a suspension of cyanoacetamide (0.84 g, 0.010 mole) and sodium hydride (0.25 g, 0.010 mole) in THF (50 ml), and, with constant stirring heated at 50° C. for 15 hours and cooled. The mixture was brought to pH 6 with acetic acid and concentrated. The residue was dissolved in $CH_2Cl_2$, extracted with 5% $NaHCO_3$, washed with brine, separated, dried ($MgSO_4$) and filtered. Concentration on the rotary evaporator gave a yellow gum which upon trituration with $Et_2O$ solidified. Recrystallization (EtOAC) gave 1.37 g, m.pt. 208°–210° C. The HPLC (u Bondpack CN column, 55% MEOH/45% $H_2O$) showed two peaks in roughly a 40:60 ratio).

In a similar manner, by substituting the appropriate intermediates and by substantially following the procedures of examples 2–5, the following compounds may be produced.

5-(4-pyridoyl)-6-ethyl-2-oxo-1,2-dihydro-3-pyridine-carbonitrile;

5-(2-thienoyl)-6-ethyl-2-oxo-1,2-dihydro-3-pyridine-carbonitrile;

5-[2-(1H-pyrroyl)]-6-ethyl-2-oxo-1,2-dihydro-3-pyridine-carbonitrile;

5-(3-furanoyl)-6-ethyl-2-oxo-1,2-dihydro-3-pyridine-carbonitrile;

5-(2-pyridoyl)-6-ethyl-2-oxo-1,2-dihydro-3-pyridine-carbonitrile;

5-(4-methoxybenzoyl)-6-ethyl-2-oxo-1,2-dihydro-3-pyridine-carbonitrile;

5-(4-methylbenzoyl)-6-ethyl-2-oxo-1,2-dihydro-3-pyridine-carbonitrile;

5-(4-nitrobenzoyl)-6-ethyl-2-oxo-1,2-dihydro-3-pyridine-carbonitrile;

5-(4-aminobenzoyl)-6-ethyl-2-oxo-1,2-dihydro-3-pyridine-carbonitrile;

5-(2,4-dichlorobenzoyl)-6-ethyl-2-oxo-1,2-dihydro-3-pyridine-carbonitrile;

5-(4-methylthiobenzoyl)-6-ethyl-2-oxo-1,2-dihydro-3-pyridine-carbonitrile; and the 6-methyl homologs thereof.

EXAMPLE 6

5-Benzoyl-1,2-dihydro-6-methyl-2-oxo-3-pyridinecarboxamide

Admix 80 ml 35% hydrochloric acid and 20 g (0.078 mole) of 5-benzoyl-1,2-dihydro-6-methyl-2-oxo-3-pyridine carbonitrile, stir the mixture at 40° C. for 5 hours, cool, and dilute the resulting mixture with 80 ml water. Collect the title compound as a precipitate.

In a similar manner, by utilizing the named 2-oxo-1,2-dihydro-3-pyridine-carbonitriles enumerated after Example 5 and by treating said compounds in accordance with the teachings of Example 6, the 3-position nitrile may be converted to the corresponding amide to produce:

5-(4-pyridoyl)-6-ethyl-2-oxo-1,2-dihydro-3-pyridine-carboxamide;

5-(2-thienoyl)-6-ethyl-2-oxo-1,2-dihydro-3-pyridine-carboxamide;

5-[2-(1H-pyrroyl)]-6-ethyl-2-oxo-1,2-dihydro-3-pyridine-carboxamide;

5-(3-furanoyl)-6-ethyl-2-oxo-1,2-dihydro-3-pyridine-carboxamide;

5-(2-pyridoyl)-6-ethyl-2-oxo-1,2-dihydro-3-pyridine-carboxamide;

5-(4-methoxybenzoyl)-6-ethyl-2-oxo-1,2-dihydro-3-pyridine-carboxamide;

5-(4-methylbenzoyl)-6-ethyl-2-oxo-1,2-dihydro-3-pyridine-carboxamide;

5-(4-nitrobenzoyl)-6-ethyl-2-oxo-1,2-dihydro-3-pyridine-carboxamide;

5-(4-aminobenzoyl)-6-ethyl-2-oxo-1,2-dihydro-3-pyridine-carboxamide;

5-(2,4-dichlorobenzoyl)-6-ethyl-2-oxo-1,2-dihydro-3-pyridine-carboxamide;

5-(4-methylthiobenzoyl)-6-ethyl-2-oxo-1,2-dihydro-3-pyridine-carboxamide; and the 6-methyl homologs thereof.

EXAMPLE 7

5-Benzoyl-1,2-dihydro-6-methyl-2-oxo-3-aminopyridine

Admix a solution of 2.5 g (0.01 mole) 5-benzoyl-1,2-dihydro-6-methyl-2-oxo-3-pyridine carboxamide in 50 ml methanol with sodium methoxide in 90 ml methanol. To the resulting mixture add, with thouough mixing, 1.6 g (0.01 mole) of bromine. Heat the resulting solution on the steam bath for 10 minutes. After which render it just acidic with acetic acid. Remove the methanol, wash the product with water to remove the sodium bromide, recrystallize the residue from ethanol to give the urethane. Mix the urethane with 7 g calcium oxide and 3 ml $H_2O$, heat the mixture to 100° C. for 2 hours, cool, and dilute with water, and extract the mixture with ethyl acetate. Water wash and dry the extract. Evaporate off the solvent to give the title compound.

In a similar manner by utilizing the named 2-oxo-1,2-dihydro-3-pypridinecarboxamides enumerated after Example 6 and by treating those compounds in accordance with the process of Example 7, the carboxamide may be converted to the corresponding amine to produce:

5-(4-pyridoyl)-6-ethyl-2-oxo-1,2-dihydro-3-aminopyridine;
5-(2-thienoyl)-6-ethyl-2-oxo-1,2-dihydro-3-aminopyridine;
5-[2-(1H-pyrroyl)]-6-ethyl-2-oxo-1,2-dihydro-3-aminopyridine;
5-(3-furanoyl)-6-ethyl-2-oxo-1,2-dihydro-3-aminopyridine;
5-(2-pyridoyl)-6-ethyl-2-oxo-1,2-dihydro-3-aminopyridine;
5-(4-methoxybenzoyl)-6-ethyl-2-oxo-1,2-dihydro-3-aminopyridine;
5-(4-methylbenzoyl)-6-ethyl-2-oxo-1,2-dihydro-3-aminopyridine;
5-(4-nitrobenzoyl)-6-ethyl-2-oxo-1,2-dihydro-3-aminopyridine;
5-(4-aminobenzoyl)-6-ethyl-2-oxo-1,2-dihydro-3-aminopyridine;
5-(2,4-dichlorobenzoyl)-6-ethyl-2-oxo-1,2-dihydro-3-aminopyridine;
5-(4-methylthiobenzoyl)-6-ethyl-2-oxo-1,2-dihydro-3-aminopyridine;

EXAMPLE 8

5-Benzoyl-6-methyl-2(1H)-pyridinone

5-Benzoyl-1,2-dihydro-6-methyl-2-oxo-3-pyridinecarbonitrile (2.32 g, 0.013 mole) and concentrated HCl (50 ml) are heated and stirred at reflux under an argon atmosphere for 5 hours. Upon cooling to room temperature a solid precipitates. The solid is collected by filtration and allowed to air dry. The dry solid is heated to 280°–290° C. and maintained at this temperature for 7 minutes. The residue is allowed to cool to room temperature then extracted into methylene chloride. Concentration of the methylene chloride solution followed by flash chromatography (50% methylene chloride - ethyl acetate) gives the title compound.

In a similar manner by utilizing the named 2-oxo-1,2-dihydro-3-pyridinecarbonitriles enumerated after Example 5 and by treating said compounds in accordance with the foregoing procedure, the 3-cyano may be converted to the corresopnding 3-H compound to produce:

5-(4-pyridoyl)-6-ethyl-2(1H)-pyridinone;
5-(2-thienoyl)-6-ethyl-2(1H)-pyridinone;
5-[2-(1H-pyrroyl)]-6-ethyl-2(1H)-pyridinone;
5-(3-furanoyl)-6-ethyl-2(1H)-pyridinone;
5-(2-pyridoyl)-6-ethyl-2(1H)-pyridinone;
5-(4-methoxybenzoyl)-6-ethyl-2(1H)-pyridinone;
5-(4-methylbenzoyl)-6-ethyl-2(1H)-pyridinone;
5-(4-nitrobenzoyl)-6-ethyl-2(1H)-pyridinone;
5-(4-aminobenzoyl)-6-ethyl-2(1H)-pyridinone;
5-(2,4-dichlorobenzoyl)-6-ethyl-2(1H)-pyridinone;
5-(4-methylthiobenzoyl)-6-ethyl-2(1H)-pyridinone
and their 6-methyl homologs.

EXAMPLE 9

5-Benzoyl-1,2-dihydro-6-methyl-2-oxo-3-pyridinecarboxylic acid

To 100 ml 6N hydrochloric acid is added 5.0 grams (0.028 mole) of 5-benzoyl-1,2-dihydro-6-methyl-2-oxo-3-pyridinecarbonitrile. The mixture is stirred and refluxed for 20 hours. Evaporation of the solvent affords the title compound.

In a similar manner, by utilizing the named 2-oxo-1,2-dihydro-3-pyridinecarbonitriles following Example 5 and by treating said compounds according to the foregoing procedure the 3-cyano compound may be converted to the corresponding 3-carboxyl compounds as follows:

5-(4-pyridoyl)-6-ethyl-2-oxo-1,2-dihydro-3-pyridinecarboxylic acid;
5-(2-thienoyl)-6-ethyl-2-oxo-1,2-dihydro-3-pyridinecarboxylic acid;
5-[2-(1H-pyrroyl)]-6-ethyl-2-oxo-1,2-dihydro-3-pyridinecarboxylic acid;
5-(3-furanoyl)-6-ethyl-2-oxo-1,2-dihydro-3-pyridinecarboxylic acid;
5-(2-pyridoyl)-6-ethyl-2-oxo-1,2-dihydro-3-pyridinecarboxylic acid;
5-(4-methoxybenzoyl)-6-ethyl-2-oxo-1,2-dihydro-3-pyridinecarboxylic acid;
5-(4-methylbenzoyl)-6-ethyl-2-oxo-1,2-dihydro-3-pyridinecarboxylic acid;
5-(4-nitrobenzoyl)-6-ethyl-2-oxo-1,2-dihydro-3-pyridinecarboxylic acid;
5-(4-aminobenzoyl)-6-ethyl-2-oxo-1,2-dihydro-3-pyridinecarboxylic acid;
5-(2,4-dichlorobenzoyl)-6-ethyl-2-oxo-1,2-dihydro-3-pyridinecarboxylic acid;
5-(4-methylthiobenzoyl)-6-ethyl-2-oxo-1,2-dihydro-3-pyridinecarboxylic acid
and their 6-methyl homologs.

EXAMPLE 10

5-Benzoyl-1,2-dihydro-6-methyl-2-oxo-3-pyridinecarboxylic Acid Ethylester

In 500 ml absolute alcohol is dissolved 5 grams 5-benzoyl-1,2-dihydro-6-methyl-2-oxo-3-pyridinecarboxylic acid. The mixture is stirred and refluxed while a slow stream of dry hydrogen chloride is introduced. The reaction is allowed to proceed for 7 hours after which the solvent is evaporated and the residue is recrystallized from alcohol to give the title compound.

In a similar manner by utilizing the named compounds following Example 9 an by following the procedures of this example, the 3-carboxylic moiety may be esterified to produce:

5-(4-pyridoyl)-6-ethyl-2-oxo-1,2-dihydro-3-pyridinecarboxylic acid ethyl ester;
5-(2-thienoyl)-6-ethyl-2-oxo-1,2-dihydro-3-pyridinecarboxylic acid ethyl ester;
5-[2-(1H-pyrroyl)]-6-ethyl-2-oxo-1,2-dihydro-3-pyridinecarboxylic acid ethyl ester;
5-(3-furanoyl)-6-ethyl-2-oxo-1,2-dihydro-3-pyridinecarboxylic acid ethyl ester;
5-(2-pyridoyl)-6-ethyl-2-oxo-1,2-dihydro-3-pyridinecarboxylic acid ethyl ester;
5-(4-methoxybenzoyl)-6-ethyl-2-oxo-1,2-dihydro-3-pyridinecarboxylic acid ethyl ester;
5-(4-methylbenzoyl)-6-ethyl-2-oxo-1,2-dihydro-3-pyridinecarboxylic acid ethyl ester;
5-(4-nitrobenzoyl)-6-ethyl-2-oxo-1,2-dihydro-3-pyridinecarboxylic acid ethyl ester;
5-(4-aminobenzoyl)-6-ethyl-2-oxo-1,2-dihydro-3-pyridinecarboxylic acid ethyl ester;
5-(2,4-dichlorobenzoyl)-6-ethyl-2-oxo-1,2-dihydro-3-pyridinecarboxylic acid ethyl ester;
5-(4-methylthiobenzoyl)-6-ethyl-2-oxo-1,2-dihydro-3-pyridinecarboxylic acid ethyl ester,
and their 6-methyl homologs.

EXAMPLE 11

3,6-Dimethyl-5-acetyl-1,2-dihydro-2-oxo-pyridine

Step A:
5-Acetylethyleneketal-1,2-dihydro-6-methyl-2-oxo-3-pyridinecarboxaldehyde To toluene (100 ml) add 5-acetyl-1,2-dihydro-6-methyl-2-oxo-3-pyridinecarbonitrile (17.6 g/0.1 mol), thyleneglycol (6.2 g/0.1 mol) and p-toluenesulfonic acid (0.1 g), and heat, under reflux conditions, the resulting mixture until the theoretical amount of water is distilled. Cool and wash the solvent with sodium bicarbonate solution. Dry (with sodium sulfate) and evaporate the solvent and dissolve the residue in 100 ml THF. The resulting solution is treated at room temperature with diisobutylaluminum hydride (0.1 mol) for one hour and the reaction mixture quenched with water and extracted with ether. The ether extract is water-washed, dried and evaporation of the solvent yields the desired product of this step.

Step B:
5-Acetyl-1,2-dihydro-3,6-dimethyl-2-oxo-pyridine

In 150 ml of ethanol, dissolve 10 g (0.045 mol) of the product of Step A and 1.0 g of 10% palladium on carbon. The resulting mixture is hydrogenated at 50° C. until 2 equivalents of hydrogen gas is taken up. The solution is filtered and the solvent is treated with 150 ml 6N hydrochloric acid and heated to reflux for one hour. Evaporation of the solvent yields the desired compound of this example.

In a similar manner, by substituting the 3-cyano compounds listed after Example 5 and by substantially following the procedure of the foregoing example, the following compounds may be prepared:

5-(4-pyridoyl)-6-ethyl-3-methyl-1,2-dihydro-2-oxopyridine;
5-(2-thienoyl)-6-ethyl-3-methyl-1,2-dihydro-2-oxopyridine;
5-[2-(1H-pyrroyl)]-6-ethyl-3-methyl-1,2-dihydro-2-oxopyridine;
5-(3-furanoyl)-6-ethyl-3-methyl-1,2-dihydro-2-oxopyridine;
5-(2-pyridoyl)-6-ethyl-3-methyl-1,2-dihydro-2-oxopyridine;
5-(4-methoxybenzoyl)-6-ethyl-3-methyl-1,2-dihydro-2-oxopyridine;
5-(4-methylbenzoyl)-6-ethyl-3-methyl-1,2-dihydro-2-oxopyridine;
5-(4-nitrobenzoyl)-6-ethyl-3-methyl-1,2-dihydro-2-oxopyridine;
5-(4-aminobenzoyl)-6-ethyl-3-methyl-1,2-dihydro-2-oxopyridine;
5-(2,4-dichlorobenzoyl)-6-ethyl-3-methyl-1,2-dihydro-2-oxopyridine;
5-(4-methylthiobenzoyl)-6-ethyl-3-methyl-1,2-dihydro-2-oxopyridine,
and the 3-$C_{2-6}$ alkyl homologs thereof.

The compounds of general formula 1 may be used in the treatment of cardiac failure including congestive heart failure, backward heart failure, forward heart failure, left ventricular heart failure, or right ventricular heart failure or in the treatment of any other condition which requires the strengthening of heart action with a cardiotonic.

The utility of formula 1 compounds as cardiotonics may be determined by administering the test compound (0.01–10 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) introducing polyethylene catheters filled 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. Heart failure is induced by administering sodium pentobarbital (20 to 40 mg/kg) followed by a continuous infusion of 1–2 mg/kg/min. of propranalol hydrochloride (4 mg/kg) followed by a continuous infusion of 0.18 mg/kg/min. to the blood perfusing the heart. Following administration of either of these cardiac depressants, the right atrial pressure dramatically increases and cardiac output is severely depressed. Reversal of these effects by the test compound indicates cardiotonic activity.

The compounds may be administered in various manners to achieve the desired effect. The compounds may be administered alone or in the form of pharmaceutical preparations to the patient being treated either orally or parenterally, that is, intravenously or intramuscularly. The amount of compound administered will vary with the patient, the severity of the cardiac failure and the mode of administration.

For oral or parenteral administration the cardiotonically effective amount of compound is from about 0.01 mg/kg or patients body weight per day up to about 500 mg/kg of patient body weight per day and preferably from about 0.10 mg/kg of patient body weight per day up to about 200 mg/kg of patient body weight per day.

For oral administration a unit dosage may contain, for example, from 1.0 to 750 mg of the active ingredient, preferably about 10 to 250 mg of the active ingredient. For parenteral administration a unit dosage may contain, for example, from 5 to 500 mg of the active ingredient, preferably about 10 to 250. Repetitive daily administration of the compounds may be desired and will vary with the condition of the patient and the mode of administration.

As used herein the term patient is taken to mean warm blooded animals, particularly mammals, such as humans.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water, alcohols, oils and other acceptable organic solvents with or without the addition of a surfactant and other pharmaceutically acceptable adjuvants. Illustrative of oils which can be employed in these preparations are those of petrolium, animal, vegetable, or synthetic origin, for example, peanut oil, soybean oil and mineral oil. In general, water, saline, aqueous dextrose and related sugar solutions, ethanol and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a solicone rubber manufactured by the Dow-Corning Corporation.

As is true in many large classes of compounds certain subgeneric members and certain specific members of the class are preferred for the pharmaceutical activity in treating disease states in man. In this instance the preferred compounds of formula I are those wherein $R_5$ is either phenyl or X-substituted phenyl and $R_6$ is methyl or ethyl. The preferred $R_3$ substituent is cyano or amino. The preferred $R_4$ substituent is hydrogen.

We claim:

1. A compound of the formula

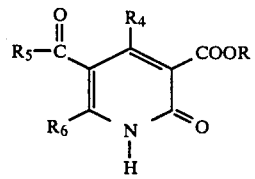

and the pharmaceutically acceptable salts thereof, wherein
R is hydrogen or lower alkyl,
$R_4$ is hydrogen or lower alkyl,
$R_5$ is phenyl or X-substituted phenyl with X being lower alkyl, lower alkoxy, lower alkylthio, halogen, nitro, lower alkanoyl, -COO (lower alkyl)-, carboxy, cyano, $NH_2$, $CONH_2$, amidino, imidazol-2-yl, and $CF_3$, and
$R_6$ is hydrogen, methyl, or ethyl.

2. A compound of claim 1 wherein $R_5$ is phenyl.
3. A compound of claim 1 wherein $R_6$ is methyl.
4. A compound of claim 1 wherein $R_6$ is ethyl.
5. A compound of claim 1 wherein $R_5$ is 4-lower alkylthio substituted phenyl.
6. A method of treating cardiac failure in a patient in need thereof which comprises administering to said patient a cardiotonically effective amount of a compound of the formula

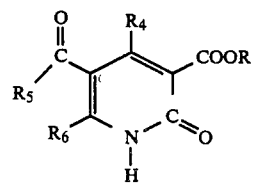

wherein
R is hydrogen or lower alkyl,
$R_4$ is a hydrogen or lower alkyl,
$R_5$ is phenyl or X-substituted phenyl with X being lower alkyl, lower alkoxy, lower alkylthio, halogen, nitro, lower alkanoyl, carboxy, cyano, $-NH_2$, $CONH_2$, amidino, imidazol-2-yl, and $CF_3$, and
$R_6$ is hydrogen, methyl, or ethyl or a pharmaceutically acceptable salt thereof.

* * * * *